United States Patent
Evans et al.

[11] Patent Number: 5,661,302
[45] Date of Patent: Aug. 26, 1997

[54] METHOD OF QUATITATIVELY DETERMINING ONE OR MORE CHARACTERISTICS OF A SUBSTANCE

[75] Inventors: Peter Dilwyn Evans; Nicholas Barnett, both of Cardiff, United Kingdom

[73] Assignee: Johnson & Johnson Medical, Inc., Arlington, Tex.

[21] Appl. No.: 697,386

[22] Filed: Aug. 23, 1996

[30] Foreign Application Priority Data

Aug. 24, 1995 [GB] United Kingdom ............. 9517366

[51] Int. Cl.$^6$ ..................................................... A61B 5/00
[52] U.S. Cl. .................. 250/339.12; 250/339.02; 128/633
[58] Field of Search ................ 250/339.12, 339.02; 128/633

[56] References Cited

U.S. PATENT DOCUMENTS 5,285,783  2/1994  Secker .................... 128/633
5,379,764  1/1995  Barnes et al. ............ 250/339.12
5,517,987  5/1996  Tsuchiya .................. 128/633
5,529,065  6/1996  Tsuchiya .................. 128/633

*Primary Examiner*—Michael J. Tokar
*Assistant Examiner*—Virgil O. Tyler

[57] ABSTRACT

Method of quantitatively determining one or more characteristics of a substance using near infrared spectroscopy. The method including irradiating a point of the substance with radiation at at least two distinct wavelengths, measuring the intensity of the radiation detected at two locations, determining the optical path lengths of the radiation between the irradiation point and the two detecting locations, and determining the effect of the divergence of the radiation reaching two locations. The relative coupling efficiencies of the two detectors are determined by the use of a second emission point equidistant from the two detectors. The characteristic being measured is then determined by the intensity of the radiation detected at the detecting locations with the result modified by accounting for the optical path lengths to the detecting locations, the detector coupling efficiencies and the effect of divergence of the radiation before reaching the detecting locations.

11 Claims, 2 Drawing Sheets

METHOD OF QUATITATIVELY DETERMINING ONE OR MORE CHARACTERISTICS OF A SUBSTANCE

This invention relates to a method of quantitatively determining one or more characteristics of a substance using near infrared spectroscopy.

Near Infrared Spectroscopy (NIRS) has been used for monitoring tissue haemoglobin and cytochrome (chromophores) for over 20 years but devices have been limited to monitoring only changes in concentration. There has been no method for quantifying the baseline from which these changes take place.

The majority of work in NIRS has concentrated on monitoring changes in brain oxygenation and haemodynamics. The problems that have prevented absolute quantification of brain chromophores include:
1. Inability to measure the coupling of light into the tissue at the emitter-tissue interface;
2. Inability to take account of the numerous background absorbers in the overlying scalp and skull tissues;
3. Neglecting to account for background absorbers in the brain tissue;
4. Neglecting to account for the optical path length of photons through the tissue;
5. Inability to measure the coupling of light from the tissue to the detector at the tissue-detector interface.

It is known to use a method for measuring path length of a beam of near infrared light passing through various tissues by a direct photon time of flight measurement. The paper published by D. T. Delpy et al in Phys. Med. Biol. 1988, Vol. 33, No. 12, 1433–1442 is incorporated herein by reference. (See also papers published by J. S. Wyatt (1989) and Essenpreis et al (1993) incorporated herein by reference). The results of such a method confirm that it is feasible to predict an average path length of photons in the head of a human, from knowledge of the spacing of the radiation emitter and detector. The knowledge of the path length is not, however, sufficient to facilitate quantified chromophore concentration measurement. Within the light path there are unpredictable intensity reducing factors which will decrease the intensity of light measured at the detector (e.g. skin, pigmentation, bone, meninges, emitter and detector coupling efficiencies). The above method for measuring path length is used in a single channel tissue spectroscopy system where the measurement of quantified change is achievable.

A dual channel tissue spectroscopy system is intended to allow dynamic cancellation of these superficially positioned effects in order to allow reliable measurement of the oxygen supply deep within the cerebral cortex.

The advantages of the present invention are based on the following points:
1. The method is based on absorption spectra from published data.
2. By adopting a two detector approach a measure for the attenuation of light at the emitter-tissue interface is no longer needed. By taking the ratio of the light intensity reaching the two detectors the measurement is not affected by light coupling.
3. The two detector approach effectively deletes the contribution to the overall signal from the scalp and skull tissue, therefore the constant background absorbers in these tissues (e.g. melanin) do not need to be accounted for.
4. In the brain tissue the main constant background absorber is water which accounts for approximately 85% of the total tissue volume. This has to be accounted for in the calculation in order to achieve absolute quantification.
5. An estimate for optical path length is needed in order to achieve absolute quantification for the different chromophores. There is published work that gives a mean optical path length for photons passing through adult or neonate heads. This is incorporated into the calculation.
6. For a two channel device to operate correctly the coupling of light at each detector has to be matched. The known device does not take this into account. The present invention does this by including a light emitting diode (LED) midway between the detectors.
7. The present invention takes into account the difference in the detected light at the two detectors due to the natural divergence of light from the emitter.

In essence the calculation is derived from first principles. No calibration is required.

As the known two channel device does not account for light divergence, constant background absorbers, or optical path length, the known device relied on a calibration procedure in which a specific contribution from the venous and arterial compartments in the tissue sample volume was assumed.

According to the present invention there is provided a method of quantitatively determining one or more characteristics of a substance by measurement of radiation absorption spectra of the substance, the method comprising:
i) irradiating a point of the substance with radiation at at least two distinct wavelengths ($\lambda_1$, $\lambda_2$);
ii) measuring the intensity of the radiation ($I_{t1}$, $I_{t2}$) detected at two locations (D1, D2);
iii) estimating the optical path lengths of the radiation between the irradiation point and the two detecting locations;
iv) determining the effect of the divergence of the radiation reaching the two locations;
v) determining the characteristic based on the intensity of the radiation detected at the detecting locations; and
vi) modifying the result by accounting for the optical path lengths to the detecting locations and the effect of divergence of the radiation before reaching the detecting locations.

Preferably, the method includes determining the relative coupling efficiencies of detectors at the detecting locations (D1, D2) by use of an emitter positioned equidistant between the detecting locations (D1, D2) and, preferably, step vi) includes modifying the result by accounting for the effect of the relative detector coupling efficiencies.

Preferably, a factor is accounted for when determining the characteristic, the factor relating to radiation absorbers present in the substance other than that of the characteristic being measured and an absorption offset is subtracted from the detected radiation intensities.

A ratio of the intensities of the detected radiation at the two detecting locations may be taken, removing a need for a measure of the attenuation of the-radiation at the point of irradiation.

A factor may be accounted for when determining the characteristic being measured, the factor relating to the relative coupling efficiency of detectors at the detecting locations.

Preferably, the effect of divergence of the radiation detected at the two detecting locations is $1/d^2$, wherein d is the optical path length to each detecting location from the irradiation point.

More than one characteristic may be measured by using radiation at more than two distinct wavelengths.

The substance may be part of a human or animal body and the radiation is near infrared radiation. The characteristic is the haemoglobin or cytochrome concentration of the tissue of the human or animal body.

A preferred embodiment of a method in accordance with the present invention is now described, with reference to the accompanying drawings, in which.

Figure 1:
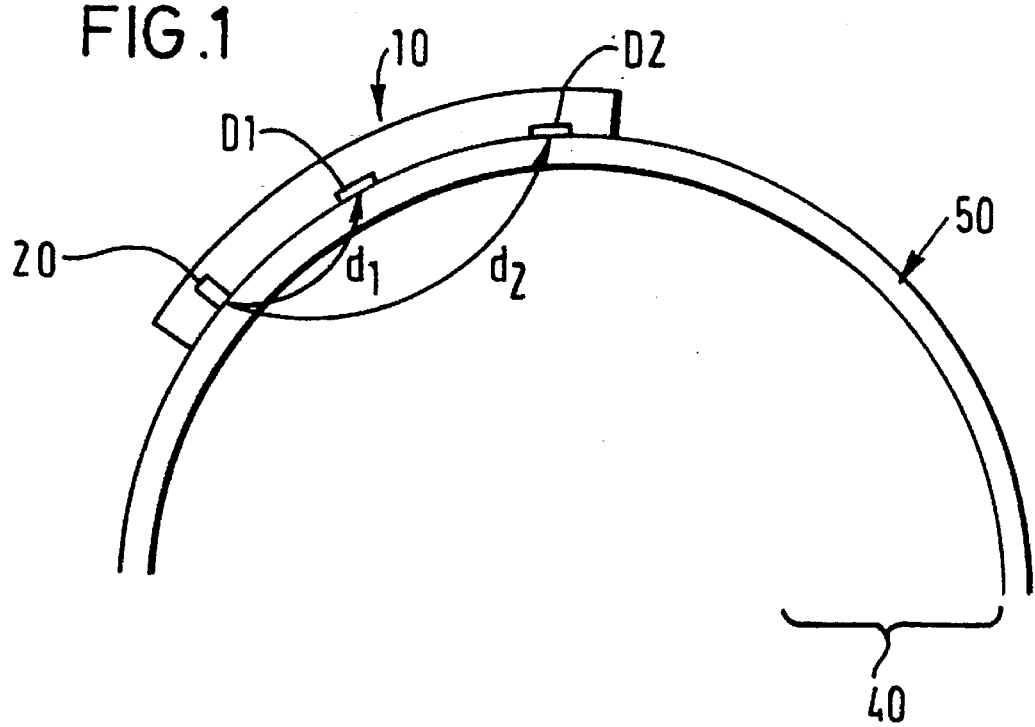
FIG. 1 is a simplified cross section of dual channel sensor placed on the surface of a human head as used in the method.

Referring to the drawings, the following terms are used to describe the method of quantitatively determining one or more characteristics of a substance. In this embodiment the substance is the tissue of the cerebral cortex.

$I_i$=Incident radiation intensity.

$I_{t1}$=Intensity of the radiation measured at detector 1 (D1).

$I_{t2}$=Intensity of the radiation measured at detector 2 (D2).

$K_1$=Coupling efficiency of the radiation source to the skin surface.

$K_2$=Coupling efficiency of the skin surface to the detectors.

$l_1 k_1 c_1$=Parameter for a collective absorbing layer 50 corresponding to skin layers, pigmentation, bone, meninges, etc. beneath the emitter 20.

$l_2 k_2 c_2$=Parameter for a collective absorbing layer corresponding to skin layers, pigmentation, bone meninges, etc. beneath each detector (D1, D2).

C=Unknown concentration of chromophore to be measured.

α=The absorption coefficient for the chromophore to be measured.

$d_1$, $d_2$=The total optical path length within the head.

$d_{11}$, $d_{21}$=The optical path length within the brain tissue.

B=A path length multiplication factor described by D. T. Delpy et al 1988.

$G_1$, $G_2$=Unknown geometry dependent factors described by D. T. Delpy et al 1988.

FIG. 1 shows a simplified cross section of a sensor 10 placed on the surface of the head over the cerebral cortex 40. For the purpose of this part of the description, it will be assumed that the characteristic is a single chromophore to be measured within the cerebral cortex 40.

This principle can be visualised in the following way:

A first optical path ($d_1$) from the emitter 20 to detector 1 (D1) is defined. As described previously, it should be possible to predict this average path length, but the unpredictable intensity reducing factors are still present.

A second optical path ($d_2$) is defined from the same emitter to detector 2 (D2). It should once again be possible to predict this different average path length, but as before unpredictable intensity reducing factors are still present.

Figure 2A:
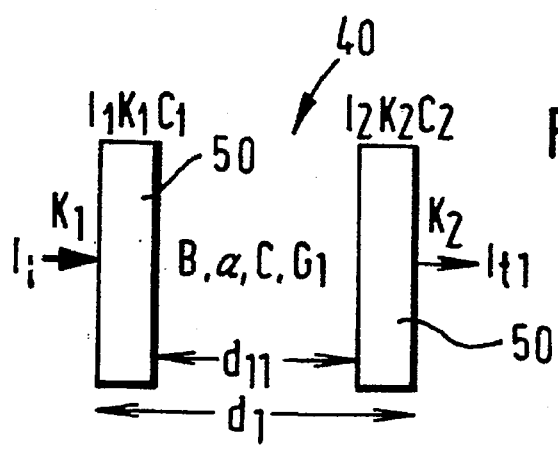
FIGS. 2a and 2b are representations of the two optical paths used in the method.
Figure 2B:
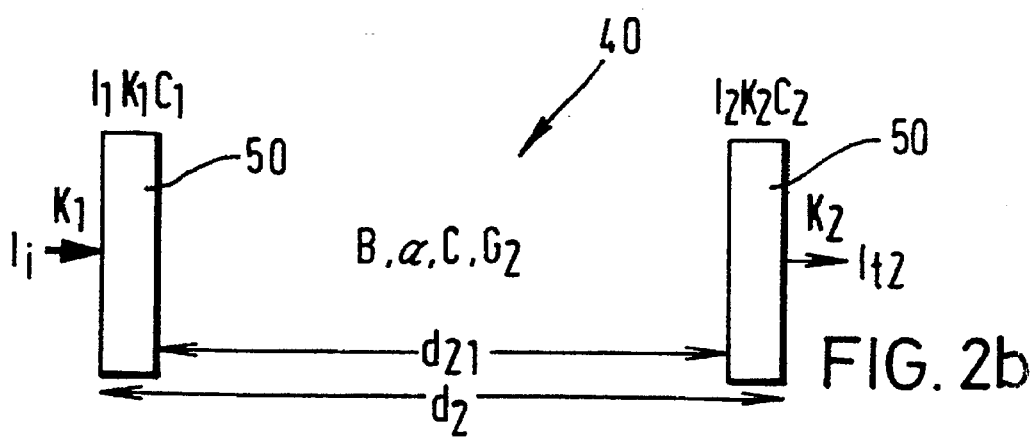

FIGS. 2a and 2b provide a representation of the two optical path lengths ($d_1$, $d_2$) of FIG. 1 which pass through an absorbing layer 50 made up of skin layers, bone, meninges etc. and through the cerebral cortex 40.

This system can be mathematically represented as follows.

PATH 1

The intensity of radiation measured at detector 1 can be defined as follows:

$$I_{t_1}=I_j.K_1.10^{-(l_1k_1c_1)}.10^{-(C\alpha d_{11}B+G_1)}.10^{-(l_2k_2c_2)}.K_2 \qquad 1$$

PATH 2

Similarly the intensity of radiation measured at detector 2:

$$I_{t_2}=I_j.K_1.10^{-(l_1k_1c_1)}.10^{-(C\alpha d_{21}B+G_2)}.10^{-(l_2k_2c_2)}.K_2 \qquad 2$$

The intensity of radiation measured at detector 2 can be defined as follows:

Dividing 2 by 1 gives the ratio of detected intensities:

$$\frac{I_{t_2}}{I_{t_1}} = \frac{I_i \cdot K_1 \cdot 10^{-(l_1k_1c_1)} \cdot 10^{-(C\alpha d_{21}B+G_2)} \cdot 10^{-(l_2k_2c_2)} \cdot K_2}{I_i \cdot K_1 \cdot 10^{-(l_1k_1c_1)} \cdot 10^{-(C\alpha d_{11}B+G_1)} \cdot 10^{-(l_2k_2c_2)} \cdot K_2} \qquad 3$$

This equation can then be simplified to:

$$\frac{I_{t_2}}{I_{t_1}} = \frac{10^{-(C\alpha d_{21}B+G_2)}}{10^{-(C\alpha d_{11}B+G_1)}} = 10^{-(C\alpha d_{21}B+G_2)+(C\alpha d_{11}B+G_1)} \qquad 4$$

Yielding after collecting terms:

$$\frac{I_{t_2}}{I_{t_1}} = 10^{-C\alpha B(d_{21}-d_{11})} \cdot 10^{(G_1-G_2)} \qquad 5$$

The path lengths used in Equation 5 are those through the brain tissue. However the path length difference is related to the calculable path difference as shown in 8.

$$d_{11}=d_1-(l_1+l_2) \qquad 6$$

$$d_{21}=d_2-(l_1+l_2) \qquad 7$$

$$d_{11}-d_{21}=d_1-d_2-(l_1+l_2)+(l_1+l_2)=d_1-d_2 \qquad 8$$

This allows 5 to be rewritten:

$$\frac{I_{t_2}}{I_{t_1}} = 10^{-C\alpha B(d_2-d_1)} \cdot 10^{(G_1-G_2)} \qquad 6$$

Equation 9 provides a relationship of the concentration of a particular chromophore C, to the measurable light intensities at detectors 1 and 2, related by its absorption coefficient and constant terms which should be fixed by the geometry of the sensor 10. This is effectively an absorption measurement which corresponds to the deep tissue of pathlength $d_2-d_1$, which is sited at the centre of path 2. (The implications of slight variations in the quality of sensor attachment will be discussed in relation to the LED coupling system described below).

This analysis can be extended to a multiple wavelength, multiple chromophore system. At this stage a two wavelength two component system is demonstrated. It is now necessary to define two chromophores of concentrations $C_1$ and $C_2$, each having wavelength sensitive absorption coefficients, defined at wavelengths $\lambda_1$ and $\lambda_2$. These will be $\alpha_{1\lambda_1}$, $\alpha_{1\lambda_2}$ respectively for substance 1 and $\alpha_{2\lambda_1}$, $\alpha_{2\lambda_2}$ for substance 2. In addition, it is also necessary to define a wavelength dependant pathlength factor for each wavelength to account for the increase in apparent pathlength with increasing wavelength due to wavelength sensitive scattering. These will now be $B_{\lambda_1}$ and $B_{\lambda_2}$.

These values may now be used to redefine the intensities measured at detectors 1 and 2 at wavelengths $\lambda_1$ and $\lambda_2$:

$$I_{t_1\lambda_1} = I_{i\lambda_1} \cdot K_1 \cdot 10^{-(l_1 k_1 c_1)\lambda_1} \cdot 10^{-(C_1\alpha_{1\lambda_1}d_{11}B_{\lambda_1}+G_{1\lambda_1})} \cdot 10^{-(C_2\alpha_{2\lambda_1}d_{11}B_{\lambda_1}+G_{1\lambda_1})} \cdot 10^{-(l_2 k_2 c_2)\lambda_1} \cdot K_2$$

$$I_{t_1\lambda_2} = I_{i\lambda_2} \cdot K_1 \cdot 10^{-(l_1 k_1 c_1)\lambda_2} \cdot 10^{-(C_1\alpha_{1\lambda_2}d_{11}B_{\lambda_2}+G_{1\lambda_2})} \cdot 10^{-(C_2\alpha_{2\lambda_2}d_{11}B_{\lambda_2}+G_{1\lambda_2})} \cdot 10^{-(l_2 k_2 c_2)\lambda_2} \cdot K_2$$

$$I_{t_2\lambda_1} = I_{i\lambda_1} \cdot K_1 \cdot 10^{-(l_1 k_1 c_1)\lambda_1} \cdot 10^{-(C_1\alpha_{1\lambda_1}d_{21}B_{\lambda_1}+G_{2\lambda_1})} \cdot 10^{-(C_2\alpha_{2\lambda_1}d_{21}B_{\lambda_1}+G_{2\lambda_1})} \cdot 10^{-(l_2 k_2 c_2)\lambda_1} \cdot K_2$$

$$I_{t_2\lambda_2} = I_{i\lambda_2} \cdot K_1 \cdot 10^{-(l_1 k_1 c_1)\lambda_2} \cdot 10^{-(C_1\alpha_{1\lambda_2}d_{21}B_{\lambda_2}+G_{2\lambda_2})} \cdot 10^{-(C_2\alpha_{2\lambda_2}d_{21}B_{\lambda_2}+G_{2\lambda_2})} \cdot 10^{-(l_2 k_2 c_2)\lambda_2} \cdot K_2$$

The deep tissue absorption's measured at each wavelength can now be represented in the form of equation 3:

$$\frac{I_{t_2\lambda_1}}{I_{t_1\lambda_1}} = \frac{I_{i\lambda_1} \cdot K_1 \cdot 10^{-(l_1 k_1 c_1)\lambda_1} \cdot 10^{-(C_1\alpha_{1\lambda_1}d_{21}B_{\lambda_1}+G_{2\lambda_1})} \cdot 10^{-(C_2\alpha_{2\lambda_1}d_{21}B_{\lambda_1}+G_{2\lambda_1})} \cdot 10^{-(l_2 k_2 c_2)\lambda_1} \cdot K_2}{I_{i\lambda_1} \cdot K_1 \cdot 10^{-(l_1 k_1 c_1)\lambda_1} \cdot 10^{-(C_1\alpha_{1\lambda_1}d_{11}B_{\lambda_1}+G_{1\lambda_1})} \cdot 10^{-(C_2\alpha_{2\lambda_1}d_{11}B_{\lambda_1}+G_{1\lambda_1})} \cdot 10^{-(l_2 k_2 c_2)\lambda_1} \cdot K_2} \qquad 10$$

$$\frac{I_{t_2\lambda_2}}{I_{t_1\lambda_2}} = \frac{I_{i\lambda_2} \cdot K_1 \cdot 10^{-(l_1 k_1 c_1)\lambda_2} \cdot 10^{-(C_1\alpha_{1\lambda_2}d_{21}B_{\lambda_2}+G_{2\lambda_2})} \cdot 10^{-(C_2\alpha_{2\lambda_2}d_{21}B_{\lambda_2}+G_{2\lambda_2})} \cdot 10^{-(l_2 k_2 c_2)\lambda_2} \cdot K_2}{I_{i\lambda_2} \cdot K_1 \cdot 10^{-(l_1 k_1 c_1)\lambda_2} \cdot 10^{-(C_1\alpha_{1\lambda_2}d_{11}B_{\lambda_2}+G_{1\lambda_2})} \cdot 10^{-(C_2\alpha_{2\lambda_2}d_{11}B_{\lambda_2}+G_{1\lambda_2})} \cdot 10^{-(l_2 k_2 c_2)\lambda_2} \cdot K_2} \qquad 11$$

These can now be simplified to the form of Equation 9 by cancelling terms and substituting for the path length difference:

$$\frac{I_{t_2\lambda_1}}{I_{t_1\lambda_1}} = \frac{10^{-(C_1\alpha_{1\lambda_1}d_{21}B_{\lambda_1}+G_{2\lambda_1})} \cdot 10^{-(C_2\alpha_{2\lambda_1}d_{21}B_{\lambda_1}+G_{2\lambda_1})}}{10^{-(C_1\alpha_{1\lambda_1}d_{11}B_{\lambda_1}+G_{1\lambda_1})} \cdot 10^{-(C_2\alpha_{2\lambda_1}d_{11}B_{\lambda_1}+G_{1\lambda_1})}} \qquad 12$$

$$= 10^{-((C_1\alpha_{1\lambda_1}d_{21}B_{\lambda_1}+G_{2\lambda_1})+(C_2\alpha_{2\lambda_1}d_{21}B_{\lambda_1}+G_{2\lambda_1})-(C_1\alpha_{1\lambda_1}d_{11}B_{\lambda_1}+G_{1\lambda_1})-(C_2\alpha_{2\lambda_1}d_{11}B_{\lambda_1}+G_{1\lambda_1}))}$$

$$= 10^{-(B_{\lambda_1}\cdot(d_{21}-d_{11})\cdot(C_1\alpha_{1\lambda_1}+C_2\alpha_{2\lambda_1})+2\cdot(G_{2\lambda_1}-G_{1\lambda_1}))}$$

$$\frac{I_{t_2\lambda_1}}{I_{t_1\lambda_1}} = 10^{-(B_{\lambda_1}\cdot(d_2-d_1)\cdot(C_1\alpha_{1\lambda_1}+C_2\alpha_{2\lambda_1})+2\cdot(G_{2\lambda_1}-G_{1\lambda_1}))}$$

$$\frac{I_{t_2\lambda_2}}{I_{t_1\lambda_2}} = \frac{10^{-(C_1\alpha_{1\lambda_2}d_{21}B_{\lambda_2}+G_{2\lambda_2})} \cdot 10^{-(C_2\alpha_{2\lambda_2}d_{21}B_{\lambda_2}+G_{2\lambda_2})}}{10^{-(C_1\alpha_{1\lambda_2}d_{11}B_{\lambda_2}+G_{1\lambda_2})} \cdot 10^{-(C_2\alpha_{2\lambda_2}d_{11}B_{\lambda_2}+G_{1\lambda_2})}} \qquad 13$$

$$= 10^{-((C_1\alpha_{1\lambda_2}d_{21}B_{\lambda_2}+G_{2\lambda_2})+(C_2\alpha_{2\lambda_2}d_{21}B_{\lambda_2}+G_{2\lambda_2})-(C_1\alpha_{1\lambda_2}d_{11}B_{\lambda_2}+G_{1\lambda_2})-(C_2\alpha_{2\lambda_2}d_{11}B_{\lambda_2}+G_{1\lambda_2}))}$$

$$= 10^{-(B_{\lambda_2}\cdot(d_{21}-d_{11})\cdot(C_1\alpha_{1\lambda_2}+C_2\alpha_{2\lambda_2})+2\cdot(G_{2\lambda_2}-G_{1\lambda_2}))}$$

$$\frac{I_{t_2\lambda_2}}{I_{t_1\lambda_2}} = 10^{-(B_{\lambda_2}\cdot(d_2-d_1)\cdot(C_1\alpha_{1\lambda_2}+C_2\alpha_{2\lambda_2})+2\cdot(G_{2\lambda_2}-G_{1\lambda_2}))}$$

Equations 12 and 13 can now be rewritten after taking Logarithms.

$$\mathrm{Log}_{10}\left(\frac{I_{t_2\lambda_1}}{I_{t_1\lambda_1}}\right) = \qquad 14$$

$$-(B_{\lambda_1}\cdot(d_2-d_1)\cdot(C_1\alpha_{1\lambda_1}+C_2\alpha_{2\lambda_1})+2\cdot(G_{2\lambda_1}-G_{1\lambda_1}))$$

$$\frac{-1}{B_{\lambda_1}\cdot(d_2-d_1)}\cdot\left(\mathrm{Log}_{10}\left(\frac{I_{t_2\lambda_1}}{I_{t_1\lambda_1}}\right)-2\cdot(G_{2\lambda_1}-G_{1\lambda_1})\right) =$$

$$C_1\alpha_{1\lambda_1}+C_2\alpha_{2\lambda_1}$$

$$\mathrm{Log}_{10}\left(\frac{I_{t_2\lambda_2}}{I_{t_1\lambda_2}}\right) = \qquad 15$$

$$-(B_{\lambda_2}\cdot(d_2-d_1)\cdot(C_1\alpha_{1\lambda_2}+C_2\alpha_{2\lambda_2})+2\cdot(G_{2\lambda_2}-G_{1\lambda_2}))$$

$$\frac{-1}{B_{\lambda_2}\cdot(d_2-d_1)}\cdot\left(\mathrm{Log}_{10}\left(\frac{I_{t_2\lambda_2}}{I_{t_1\lambda_2}}\right)-2\cdot(G_{2\lambda_2}-G_{1\lambda_2})\right) =$$

$$C_1\alpha_{1\lambda_2}+C_2\alpha_{2\lambda_2}$$

Combining equations 14 and 15 into matrix form gives:

$$\begin{bmatrix} \frac{-1}{B_{\lambda_1}\cdot(d_2-d_1)}\cdot\left(\mathrm{Log}_{10}\left(\frac{I_{t_2\lambda_1}}{I_{t_1\lambda_1}}\right)-2\cdot(G_{2\lambda_1}-G_{1\lambda_1})\right) \\ \frac{-1}{B_{\lambda_2}\cdot(d_2-d_1)}\cdot\left(\mathrm{Log}_{10}\left(\frac{I_{t_2\lambda_2}}{I_{t_1\lambda_2}}\right)-2\cdot(G_{2\lambda_2}-G_{1\lambda_2})\right) \end{bmatrix} = \qquad 16$$

$$\begin{bmatrix} \alpha_{1\lambda_1} & \alpha_{2\lambda_1} \\ \alpha_{1\lambda_2} & \alpha_{2\lambda_2} \end{bmatrix} \cdot \begin{bmatrix} C_1 \\ C_2 \end{bmatrix}$$

Multiplying both sides of Equation 16 by the inverse of the coefficient matrix:

$$\begin{bmatrix} \alpha_{1\lambda_1} & \alpha_{2\lambda_1} \\ \alpha_{1\lambda_2} & \alpha_{2\lambda_2} \end{bmatrix}^{-1} \cdot \begin{bmatrix} \frac{-1}{B_{\lambda_1} \cdot (d_2 - d_1)} \cdot \left( \text{Log}_{10}\left(\frac{I_{t_2\lambda_1}}{I_{t_1\lambda_1}}\right) - 2 \cdot (G_{2\lambda_1} - G_{1\lambda_1}) \right) \\ \frac{-1}{B_{\lambda_2} \cdot (d_2 - d_1)} \cdot \left( \text{Log}_{10}\left(\frac{I_{t_2\lambda_2}}{I_{t_1\lambda_2}}\right) - 2 \cdot (G_{2\lambda_2} - G_{1\lambda_2}) \right) \end{bmatrix} = \begin{bmatrix} \alpha_{1\lambda_1} & \alpha_{2\lambda_1} \\ \alpha_{1\lambda_2} & \alpha_{2\lambda_2} \end{bmatrix}^{-1} \cdot \begin{bmatrix} \alpha_{1\lambda_1} & \alpha_{2\lambda_1} \\ \alpha_{1\lambda_2} & \alpha_{2\lambda_2} \end{bmatrix} \cdot \begin{bmatrix} C_1 \\ C_2 \end{bmatrix}$$

$$= \begin{bmatrix} 1 & 0 \\ 0 & 1 \end{bmatrix} \cdot \begin{bmatrix} C_1 \\ C_2 \end{bmatrix}$$

$$\begin{bmatrix} \alpha_{1\lambda_1} & \alpha_{2\lambda_1} \\ \alpha_{1\lambda_2} & \alpha_{2\lambda_2} \end{bmatrix}^{-1} \cdot \begin{bmatrix} \frac{-1}{B_{\lambda_1} \cdot (d_2 - d_1)} \cdot \left( \text{Log}_{10}\left(\frac{I_{t_2\lambda_1}}{I_{t_1\lambda_1}}\right) - 2 \cdot (G_{2\lambda_1} - G_{1\lambda_1}) \right) \\ \frac{-1}{B_{\lambda_2} \cdot (d_2 - d_1)} \cdot \left( \text{Log}_{10}\left(\frac{I_{t_2\lambda_2}}{I_{t_1\lambda_2}}\right) - 2 \cdot (G_{2\lambda_2} - G_{1\lambda_2}) \right) \end{bmatrix} = \begin{bmatrix} C_1 \\ C_2 \end{bmatrix} \quad 17$$

Equation 17 defines the concentrations of the two chromophores with respect to the intensities of the two wavelengths of light measured at the two detectors. In this form it allows a solution for the concentrations of the chromophores so long as the absorption coefficients and pathlengths have been previously defined.

The principle of solving for n unknown chromophore concentrations with n wavelengths can be extended to as many chromophores as can be isolated with measurable optical absorption spectra within the optical field of the sensor so long as it is possible to resolve the individual absorption spectra within the total sum of absorptions. As described previously, to satisfy this requirement, it is necessary that any set of absorption coefficients for, an individual substance defined for the coefficient matrix, are not a linear combination of the absorption coefficients of the other components in the coefficient matrix. The failure to satisfy this requirement will lead to a matrix of absorption coefficients which cannot be inverted.

The satisfactory creation of an n component system of chromophores leads to a solution of the form:

each other out. If the coupling efficiencies are well defined it allows them to be calculated out of the final results.

Over the duration of a measurement, it is quite likely that moisture may build up under the sensor which may alter the coupling efficiencies of the two detectors independently.

This invention uses a light source 30 mounted midway between both detectors which is aimed directly into the tissue under investigation. (i.e. not preferentially directed towards either of the detectors.) This should create an illumination within the tissue the intensity of which should be the same at each detector. Using this even illumination on both detectors, the gains on the two detection channels can now be measured. This will be a combination of their optical gain together with their electronic amplification gain. This provides a ratio of the overall gains of the two channels, combined with a measure of the relative coupling efficiencies and relative superficial absorber concentrations under each detector, for example the effect of a freckle under one detector, which would effect the measured intensity, will be cancelled out. This ratio can then be applied to the division which is performed in the two channel processing algorithm to correct for any unequal gains which are present.

$$\begin{bmatrix} \alpha_{1\lambda_1} & \alpha_{2\lambda_1} & \cdots & \alpha_{n\lambda_1} \\ \alpha_{1\lambda_2} & \alpha_{2\lambda_2} & \cdots & \cdot \\ \cdot & \cdot & \cdot & \cdot \\ \cdot & \cdot & \cdot & \cdot \\ \alpha_{1\lambda_n} & \cdots & \cdots & \alpha_{n\lambda_n} \end{bmatrix}^{-1} \cdot \begin{bmatrix} \frac{-1}{B_{\lambda_1} \cdot (d_2 - d_1)} \cdot \left( \text{Log}_{10}\left(\frac{I_{t_2\lambda_1}}{I_{t_1\lambda_1}}\right) - 2 \cdot (G_{2\lambda_1} - G_{1\lambda_1}) \right) \\ \frac{-1}{B_{\lambda_2} \cdot (d_2 - d_1)} \cdot \left( \text{Log}_{10}\left(\frac{I_{t_2\lambda_2}}{I_{t_1\lambda_2}}\right) - 2 \cdot (G_{2\lambda_2} - G_{1\lambda_2}) \right) \\ \cdot \\ \cdot \\ \frac{-1}{B_{\lambda_n} \cdot (d_2 - d_1)} \cdot \left( \text{Log}_{10}\left(\frac{I_{t_2\lambda_n}}{I_{t_1\lambda_n}}\right) - 2 \cdot (G_{2\lambda_n} - G_{1\lambda_n}) \right) \end{bmatrix} = \begin{bmatrix} C_1 \\ C_2 \\ \cdot \\ \cdot \\ C_n \end{bmatrix} \quad 18$$

The details of these terms will be discussed in the following pages.

Figure 3:
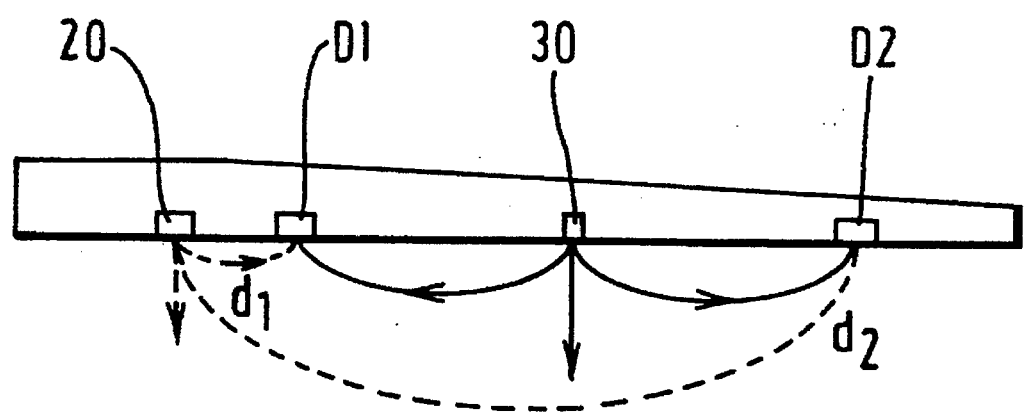
FIG. 3 is a diagrammatic representation of the coupling compensation of the method.

FIG. 3 is a representation of a sensor 10 with a light source 30 in the form of a light emitting diode (LED) provided midway between the detectors D1, D2 as described below.

The principle of operation of the previously described dual channel system relies on the optical coupling and the gains of the two detector channels being precisely matched, or else well defined. If matched, this allows the coupling efficiencies between the two channels to effectively cancel As an example of the use of this system, take the hypothetical situation where the optics of the tissue under measurement cause the light intensity per unit area falling on detector 1 to be 100 times that falling on detector 2. Under this situation, if the gains, coupling and area of detectors used for detectors 1 and 2 are the same, the signals measured on the two detection channels will be in the ratio 100:1 respectively. If now the area of detector 2 is increased to three times that of detector 1, the detected signals would be expected to be 100:3. If in addition to this the coupling efficiency and electronic gain of channel 2 are twice that of channel 1, then the signals measured will be in the ratio of 100:6. This difference of the measured signal ratio from the actual intensities per unit area which are emerging from the tissue surface will cause an error in the calculation of the chromophore concentration by a factor of $Log_{10}(6)=0.778$.

Under these conditions, the measurement of a signal emitted by the Light Emitting Diode (LED) source positioned exactly half way between the two detectors would measure signals in the ratio of 1:6 on detectors 1 and 2 respectively.

This ratio can now be used to calibrate the relative total gains between channel 1 and 2 in the following way:

$$\text{Corrected Detected Laser Signal Ratio} = \frac{\text{Laser Intensity Channel 2}}{\text{Laser Intensity Channel 1}} \times \frac{\text{LED Intensity Channel 1}}{\text{LED Intensity Channel 2}}$$

$$\left(\frac{I_{t_2 \lambda 1}}{I_{t_1 \lambda 1}}\right)_{Corr.} = \frac{6}{100} \times \frac{1}{6} = \frac{1}{100}.$$

20

This leads to a modification to Equation 18:

$$\begin{bmatrix} \alpha_{1\lambda_1} & \alpha_{2\lambda_1} & \cdots & \alpha_{n\lambda_1} \\ \alpha_{1\lambda_2} & \alpha_{2\lambda_2} & \cdots & \\ \vdots & \vdots & \ddots & \vdots \\ \alpha_{1\lambda_n} & \cdots & \cdots & \alpha_{n\lambda_n} \end{bmatrix}^{-1} \begin{bmatrix} \frac{-1}{B_{\lambda_1} \cdot (d_2 - d_1)} \cdot \left( Log_{10}\left(\frac{I_{t_2\lambda_1}}{I_{t_1\lambda_1}} \cdot \frac{I_{t_1 LED}}{I_{t_2 LED}}\right) - 2 \cdot (G_{2\lambda_1} - G_{1\lambda_1}) \right) \\ \frac{-1}{B_{\lambda_2} \cdot (d_2 - d_1)} \cdot \left( Log_{10}\left(\frac{I_{t_2\lambda_2}}{I_{t_1\lambda_2}} \cdot \frac{I_{t_1 LED}}{I_{t_2 LED}}\right) - 2 \cdot (G_{2\lambda_2} - G_{1\lambda_2}) \right) \\ \vdots \\ \frac{-1}{B_{\lambda_n} \cdot (d_2 - d_1)} \cdot \left( Log_{10}\left(\frac{I_{t_2\lambda_n}}{I_{t_1\lambda_n}} \cdot \frac{I_{t_1 LED}}{I_{t_2 LED}}\right) - 2 \cdot (G_{2\lambda_n} - G_{1\lambda_n}) \right) \end{bmatrix} = \begin{bmatrix} C_1 \\ C_2 \\ \vdots \\ \vdots \\ C_n \end{bmatrix}$$

19

Figure 4:
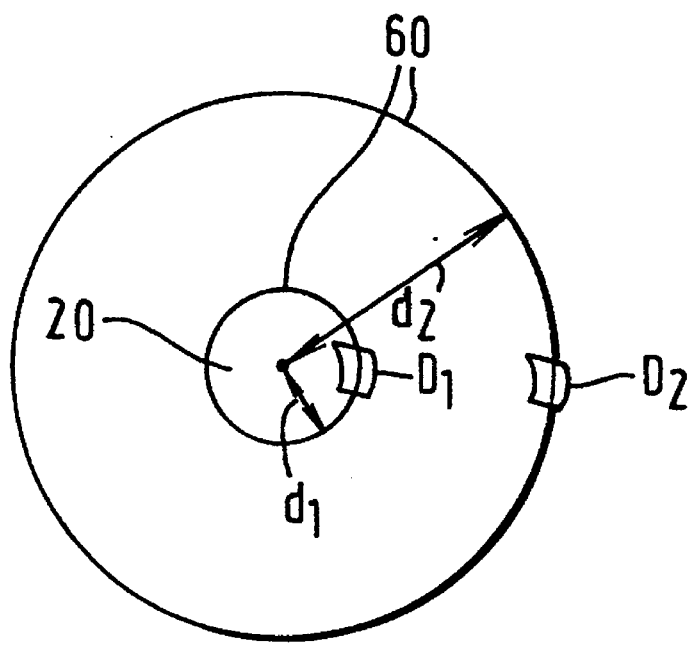
FIG. 4 is a representation of the effect of beam divergence on the detected radiation used in the method.

FIG. 4 is a representation of the effect of beam divergence on the detected intensity at detectors D1, D2.

In FIG. 4 spherical shells 60 represent the detector spacings used in the two channel system.

If a light source as used in this spectroscopy system is emitting its output uniformly in all directions at the centre of a purely scattering, (non-absorbing) spherical material, the photon flux passing through each of the spherical shells indicated on FIG. 4, will be exactly the same since eventually all photons emitted will be lost from the spherical material. If the photon flux per unit area passing through the areas indicated by Detectors 1 and 2 is measured, it will be found that each will be proportional to:

$$\frac{1}{d^2}$$

Therefore in the case demonstrated in FIG. 4, the ratio of the intensities measured by the two equal sized detectors indicated will be:

$$\frac{I_2}{I_1} = \frac{d_1^2}{d_2^2} = \left(\frac{d_1}{d_2}\right)^2$$

20

This means that even if no absorption is taking place, detectors mounted at positions radiating away from an emission source will detect decreasing intensities caused purely by beam divergence. This factor must be taken into account in order to calculate the intensity reduction which is attributable to chromophore absorption. This leads to a modification to equation 4–19:

$$\begin{bmatrix} \alpha_{1\lambda_1} & \alpha_{2\lambda_1} & \cdots & \alpha_{n\lambda_1} \\ \alpha_{1\lambda_2} & \alpha_{2\lambda_2} & \cdots & \\ \cdot & \cdot & \cdot & \cdot \\ \cdot & \cdot & \cdot & \cdot \\ \cdot & \cdot & \cdot & \cdot \\ \alpha_{1\lambda_n} & \cdots & \cdots & \alpha_{n\lambda_n} \end{bmatrix}^{-1} \cdot \begin{bmatrix} \frac{-1}{B_{\lambda_1} \cdot (d_2 - d_1)} \cdot \left( \mathrm{Log}_{10}\left( \left(\frac{d_2}{d_1}\right)^2 \cdot \frac{I_{t_2\lambda_1}}{I_{t_1\lambda_1}} \cdot \frac{I_{t_1 LED}}{I_{t_2 LED}} \right) - 2 \cdot (G_{2\lambda_1} - G_{1\lambda_1}) \right) \\ \frac{-1}{B_{\lambda_2} \cdot (d_2 - d_1)} \cdot \left( \mathrm{Log}_{10}\left( \left(\frac{d_2}{d_1}\right)^2 \cdot \frac{I_{t_2\lambda_2}}{I_{t_1\lambda_2}} \cdot \frac{I_{t_1 LED}}{I_{t_2 LED}} \right) - 2 \cdot (G_{2\lambda_2} - G_{1\lambda_2}) \right) \\ \cdot \\ \cdot \\ \cdot \\ \frac{-1}{B_{\lambda_n} \cdot (d_2 - d_1)} \cdot \left( \mathrm{Log}_{10}\left( \left(\frac{d_2}{d_1}\right)^2 \cdot \frac{I_{t_2\lambda_n}}{I_{t_1\lambda_n}} \cdot \frac{I_{t_1 LED}}{I_{t_2 LED}} \right) - 2 \cdot (G_{2\lambda_n} - G_{1\lambda_n}) \right) \end{bmatrix} = \begin{bmatrix} C_1 \\ C_2 \\ \cdot \\ \cdot \\ \cdot \\ \cdot \\ C_n \end{bmatrix} \quad 4\text{-}21$$

Up to this point, the theoretical analysis presented has assumed that the only absorbers within the measurement region within the cerebral cortex are those whose absorption coefficients have been included in the creation of the concentration calculation algorithm. The irrelevant, unknown absorbers present in the extracerebral tissues are of course deleted from the absorption measurement with the two channel deletion system. This leaves the undesired absorptions of the remaining substances within the cerebral cortex, for example:

1. Water, a fundamental constituent of almost all tissues within the body, and contributing to approximately 75 to 85 percent of the of the tissue mass within the cerebral cortex. (C. A. Keele, E. Neil 1971, Jobsis Patent)
2. Lipids and Phospholipids which make up the cell walls of all cells within the cerebral cortex.
3. Amino Acids and Proteins
4. Nucleic acids
5. Carbohydrates
6. Vitamins and Hormones
7. Ionic substances (Sodium, Calcium Potassium and Magnesium) and trace elements.

Analysis of Equation 21 reveals that the $G_2$–$G_1$ components within the equation are taking the form of an additional absorption. In the original work on single channel instruments where these factors were introduced (Delpy et al. 1988), this additional absorption would have also included the extracerebral tissues, and emitter and detector coupling efficiencies, in addition to the fixed absorbers included within the cerebral cortex. As has been already discussed, the effects of extracerebral tissues and coupling efficiencies are removed by the use of the two channel system, which then only leaves the fixed absorbers present in the cerebral cortex.

The effects of these fixed absorbers on the calculations for final chromophore concentration can be estimated. This can be done by estimating the absorption which would be caused by the quantities of substances found within the cerebral cortex, over the associated optical pathlength. This can be viewed as an absorption offset, and can be directly associated to chromophore offsets which would be measured by a dual channel tissue spectroscopy system. This absorption offset can effectively be subtracted from the signals measured by an instrument to allow a more direct measurement of the absolute chromophore concentrations within the cerebral cortex.

The method of quantitatively determining the characteristics of a substance has been described in its application to cerebral measurements. The method can also be used to non-invasively monitor tissue haemoglobin concentration in other parts of the body and may be useful in fields such as plastic surgery and vascular surgery.

Modifications and improvements can be made to the above without departing from the scope of the present invention.

We claim:

1. A method of quantitatively determining one or more characteristics of a substance by measurement of radiation absorption spectra of the substance, the method comprising:
   i) irradiating a point of the substance with radiation at at least two distinct wavelengths ($\lambda_1$, $\lambda_2$);
   ii) measuring the intensity of the radiation ($I_{t1}$, $I_{t2}$) detected at two locations (D1, D2);
   iii) estimating the optical path lengths of the radiation between the irradiation point and the two detecting locations;
   iv) determining the effect of the divergence of the radiation reaching the two locations;
   v) determining the characteristic based on the intensity of the radiation detected at the detecting locations; and
   vi) modifying the result by accounting for the optical path lengths to the detecting locations and the effect of divergence of the radiation before reaching the detecting locations.

2. A method as claimed in claim 1, wherein radiation at a further distinct wavelength is transmitted from a second point equidistant between the detecting locations, the radiation detected at the detecting locations at this wavelength being measured and used to determine the relative gain at the detecting locations.

3. A method as claimed in claim 1, wherein a factor is accounted for when determining the characteristic, the factor relating to radiation absorbers present in the substance other than that of the characteristic being measured and an absorbtion offset is subtracted from the detected radiation intensities.

4. A method as claimed in claim 1, wherein a ratio of the intensities of the detected radiation at the two detecting locations is taken, removing a need for a measure of the attenuation of the radiation at the point of irradiation.

5. A method as claimed in claim 1, wherein a factor is accounted for when determining the characteristic being measured, the factor relating to the relative coupling efficiency of detectors at the detecting locations.

6. A method as claimed in claim 1, wherein the effect of divergence of the radiation detected at the two detecting locations is $1/d^2$, wherein d is the optical path length to each detecting location from the irradiation point.

7. A method as claimed in claim 1, wherein more than one characteristic is measured by using radiation at more than two distinct wavelengths.

8. A method as claimed in claim 1, wherein the substance is part of a human or animal body and the radiation is near infrared radiation.

9. A method as claimed in claim 8, wherein the characteristic is the hemoglobin or cytochrome concentration of the tissue of the human or animal body.

10. A method as claimed in claim 8, wherein the principal tissue component radiation absorber is water.

11. A device for quantitatively determining one or more characteristics of a substance using the method of claim 1.

* * * * *